(12) United States Patent
Åberg et al.

(10) Patent No.: US 9,987,440 B2
(45) Date of Patent: Jun. 5, 2018

(54) INHALATOR FOR SUBSTANCES IN POWDER FORM

(75) Inventors: Jan Åberg, Kållered (SE); Yutaka Kataoka, Lindome (SE); Jan Hedegaard-Broch, Mölnlycke (SE); Stefan Fransson, Göteborg (SE); Ulf Rytterholm, Bålsta (SE)

(73) Assignee: Simplified Solutions Sweden AB, Lindome (SE)

( * ) Notice: Subject to any disclaimer, the term of this patent is extended or adjusted under 35 U.S.C. 154(b) by 792 days.

(21) Appl. No.: 14/006,454

(22) PCT Filed: Mar. 21, 2012

(86) PCT No.: PCT/SE2012/000039
§ 371 (c)(1),
(2), (4) Date: Sep. 20, 2013

(87) PCT Pub. No.: WO2012/128692
PCT Pub. Date: Sep. 27, 2012

(65) Prior Publication Data
US 2014/0007875 A1   Jan. 9, 2014

(30) Foreign Application Priority Data

Mar. 21, 2011 (SE) ...................................... 1130016
Oct. 26, 2011 (SE) ...................................... 1130104
Dec. 18, 2011 (SE) ...................................... 1130122

(51) Int. Cl.
*A61M 15/00* (2006.01)

(52) U.S. Cl.
CPC .... *A61M 15/0045* (2013.01); *A61M 15/0015* (2014.02); *A61M 15/0016* (2014.02);
(Continued)

(58) Field of Classification Search
CPC . A61K 9/0075; A61M 11/001; A61M 11/002; A61M 11/003; A61M 11/02;
(Continued)

(56) References Cited

U.S. PATENT DOCUMENTS 4,860,740 A    8/1989  Kirk et al.
5,492,112 A *  2/1996  Mecikalski .......... A61K 9/0075
                                                128/203.15
(Continued)

FOREIGN PATENT DOCUMENTS

EP   1172122 A1   1/2002
GB   2457615 A    8/2009
(Continued)

OTHER PUBLICATIONS

"European Application Serial No. 12760127.6, Supplementary European Search Report dated Sep. 19, 2014", 9 pgs.
(Continued)

*Primary Examiner* — Annette Dixon
(74) *Attorney, Agent, or Firm* — Schwegman Lundberg & Woessner, P.A.

(57) ABSTRACT

Disclosed herein are inhalation devices and methods for storage and release of substances in powder form such as a drug. The inhalation devices can include a plurality of powder chambers for storing a respective dose of a pre-loaded powdery substance, and an uncovering device for dispensing one dose at a time. The inhalation devices can include an advancing mechanism is arranged to feed the dose ring one powder chamber at a time. The powder chambers can be oriented in the surface of the dose ring and at least one seal is arranged to seal the powder chambers. The powder chambers can be uncovered or opened to at least (Continued)

D-D a portion of an air channel, and the content of the powder chamber is exposed to, and can pass through, the air channel by means of an air flow.

25 Claims, 13 Drawing Sheets

(52) U.S. Cl.
CPC .... *A61M 15/0026* (2014.02); *A61M 15/0048* (2014.02); *A61M 15/0075* (2014.02); *A61M 15/0043* (2014.02); *A61M 2202/064* (2013.01)

(58) Field of Classification Search
CPC .......... A61M 15/0003; A61M 15/0006; A61M 15/0008; A61M 15/0015; A61M 15/0016; A61M 15/002; A61M 15/0021; A61M 15/0025; A61M 15/0026; A61M 15/0028; A61M 15/0031; A61M 15/0033; A61M 15/0035; A61M 15/0036; A61M 15/0041; A61M 15/0043; A61M 15/0045; A61M 15/0048; A61M 15/005; A61M 15/0051; A61M 15/0055; A61M 15/0061; A61M 15/0065; A61M 15/0068; A61M 15/0071; A61M 15/0075; A61M 15/0081; A61M 15/0085; A61M 15/0091; A61M 15/02; A61M 16/0866; A61M 16/107; A61M 2016/0021; A61M 2016/0024; A61M 2016/0039; A61M 2202/062; A61M 2202/064; A61M 2205/0266; A61M 2205/071; A61M 2205/073; A61M 2205/3365; A61M 2205/50; A61M 2205/583; A61M 2205/8206; A61M 2205/8225; A61M 2206/10; A61M 2206/14; A61M 2206/16; A61M 2209/02; B65D 2583/0409; B65D 83/0454; F25J 2200/54; F25J 2240/42; F25J 3/04303; F25J 3/04309; F25J 3/04321; F25J 3/04424; G06M 1/04; G06M 1/045; G06M 1/248; Y10T 29/49826
USPC ............ 128/200.14, 200.17, 200.18, 200.23, 128/200.24, 203.12, 203.15, 203.18, 128/203.19, 203.21, 203.23, 204.13
See application file for complete search history.

(56) References Cited

U.S. PATENT DOCUMENTS

| | | | | |
|---|---|---|---|---|
| 6,065,472 A | * | 5/2000 | Anderson | A61M 15/0045 128/200.18 |
| 6,237,590 B1 | * | 5/2001 | Leedom | A61M 15/0045 128/203.12 |
| 6,273,085 B1 | | 8/2001 | Eisele et al. | |
| 6,752,148 B1 | * | 6/2004 | McGinn | A61M 15/0045 128/203.15 |
| 6,871,647 B2 | | 3/2005 | Allan et al. | |
| 7,089,935 B1 | * | 8/2006 | Rand | A61M 15/0045 128/203.15 |
| 7,219,665 B1 | * | 5/2007 | Braithwaite | A61M 15/0045 128/203.12 |
| 7,275,538 B2 | | 10/2007 | Nakamura et al. | |
| 7,395,821 B2 | | 7/2008 | Lulla et al. | |
| 7,571,724 B2 | | 8/2009 | Braithwaite | |
| 8,584,673 B2 | * | 11/2013 | Thoemmes | A61M 11/02 128/200.14 |
| 2004/0123864 A1 | * | 7/2004 | Hickey | A61M 15/0085 128/203.12 |
| 2005/0172963 A1 | | 8/2005 | Allan et al. | |
| 2005/0183723 A1 | * | 8/2005 | Pinon | A61M 15/0065 128/203.15 |
| 2006/0237010 A1 | * | 10/2006 | De Boer | A61M 15/0045 128/203.15 |
| 2007/0235029 A1 | * | 10/2007 | Zhu | A61M 15/0045 128/203.12 |
| 2009/0205657 A1 | | 8/2009 | Barney et al. | |
| 2010/0078022 A1 | | 4/2010 | Striebig et al. | |
| 2010/0180894 A1 | | 7/2010 | Jones et al. | |
| 2011/0226244 A1 | * | 9/2011 | Perkins | A61M 15/0045 128/203.15 |
| 2012/0298106 A1 | * | 11/2012 | Kjellgren | A61M 15/0045 128/203.15 |

FOREIGN PATENT DOCUMENTS

| | | |
|---|---|---|
| WO | WO-99/36116 A1 | 7/1999 |
| WO | WO-2000/045879 A1 | 8/2000 |
| WO | WO-03/090811 | 11/2003 |
| WO | WO-2003/095010 A2 | 11/2003 |
| WO | WO-2005/002654 A2 | 1/2005 |
| WO | WO-2009/102273 A1 | 8/2009 |
| WO | WO-2010/042035 A1 | 4/2010 |
| WO | WO-2011/004287 A1 | 1/2011 |
| WO | WO-2012/128692 A1 | 9/2012 |

OTHER PUBLICATIONS

"International Application No. PCT/SE2012/000039, International Preliminary Report on Patentability dated Sep. 24, 2013", 8 pgs.
"International Application No. PCT/SE2012/000039, Wriiten Opinion dated Jun. 26, 2012", 7 pgs.
"European Application Serial No. 12760127.6, Office Action dated Aug. 10, 2014", 1 pg.
"European Application Serial No. 12760127.6, Response filed Mar. 26, 2015 to Office Action dated Aug. 10, 2014", 51 pgs.
"International Application No. PCT/SE2012/000039, International Search Report dated Jun. 26, 2012", (dated Jun. 26, 2012), 6 pgs.

* cited by examiner

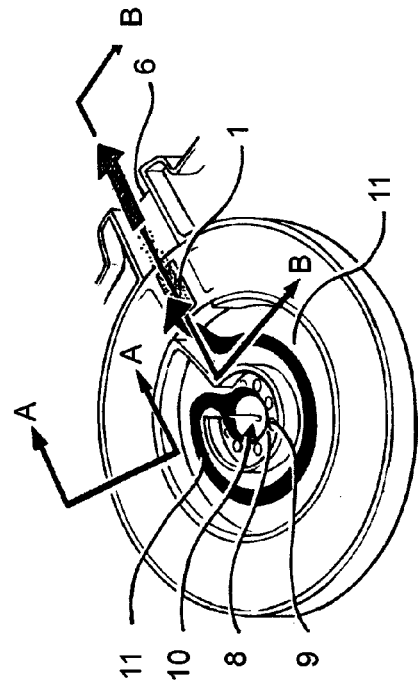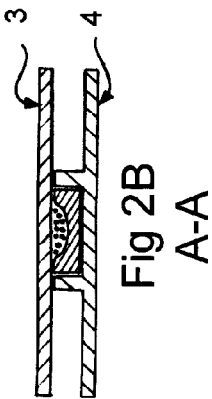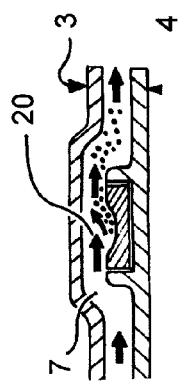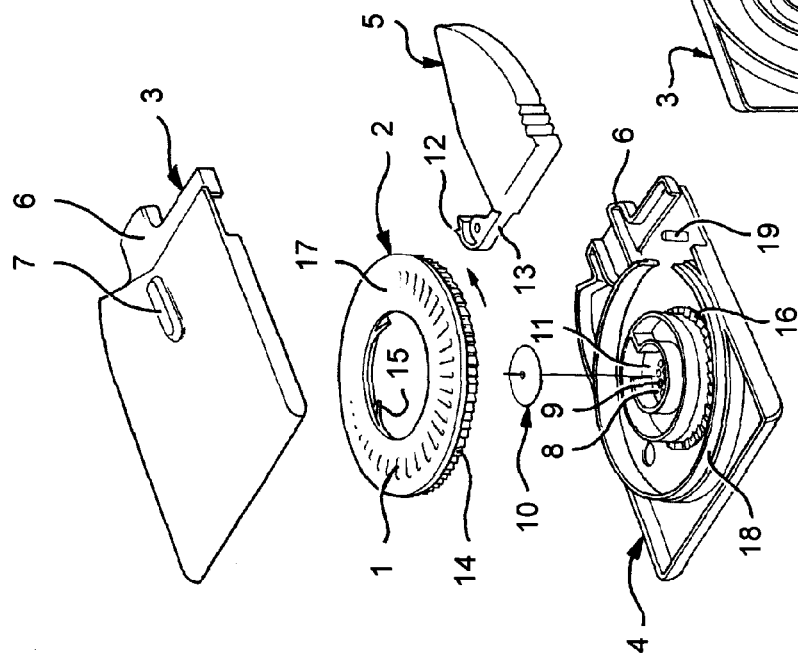

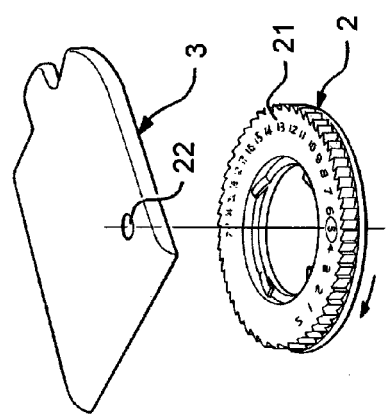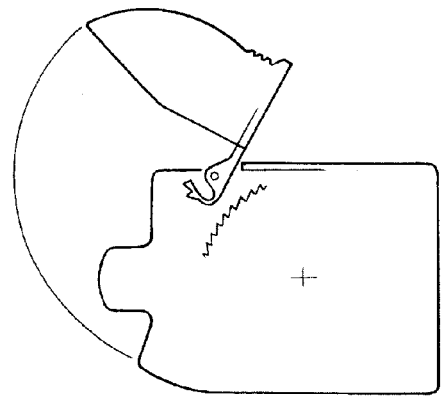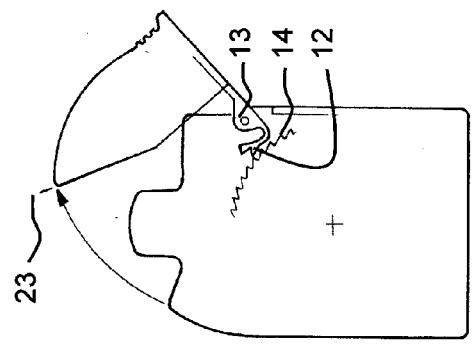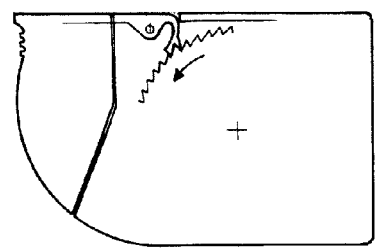

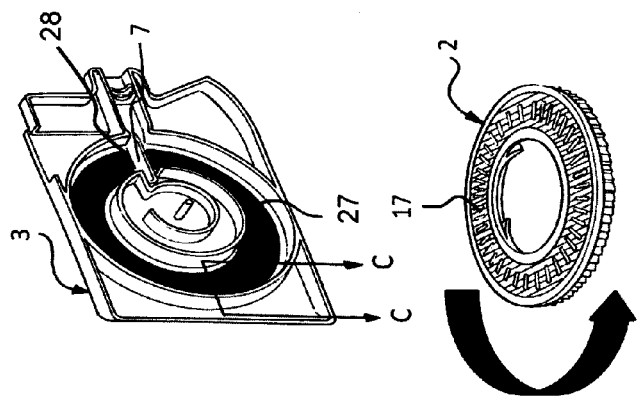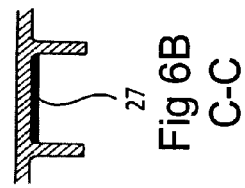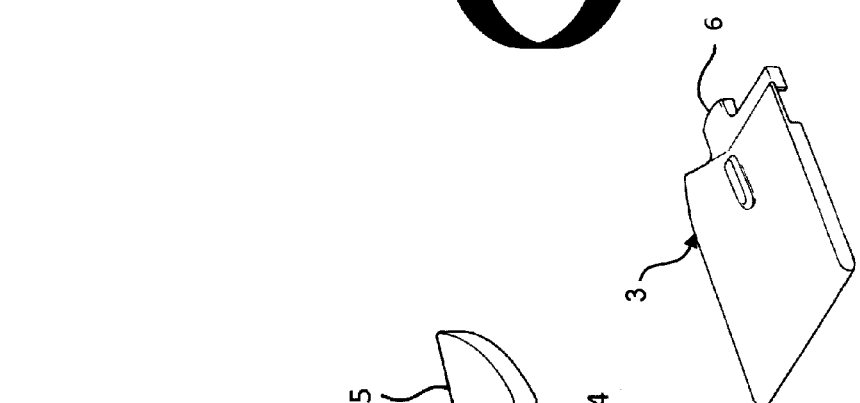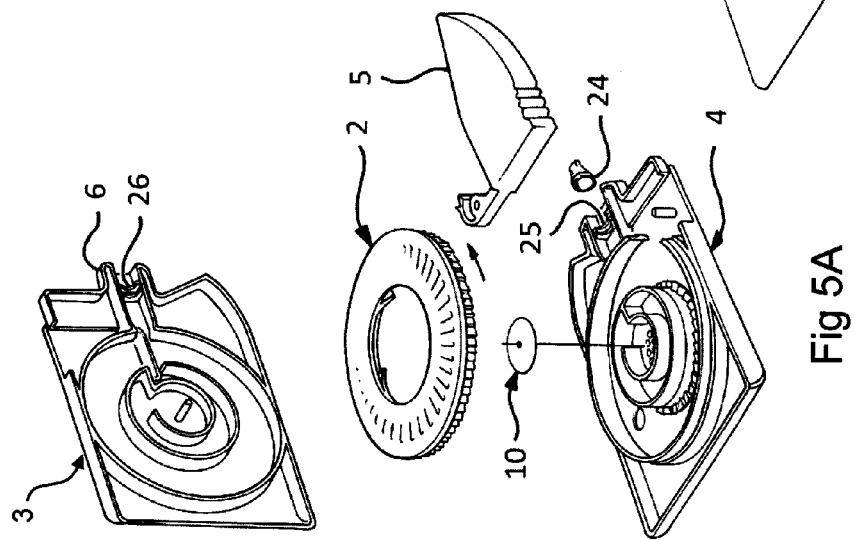

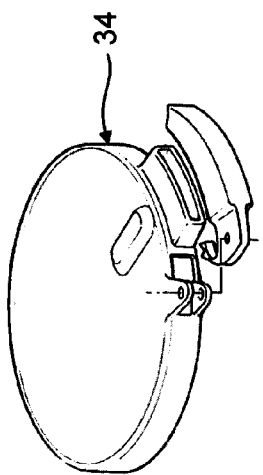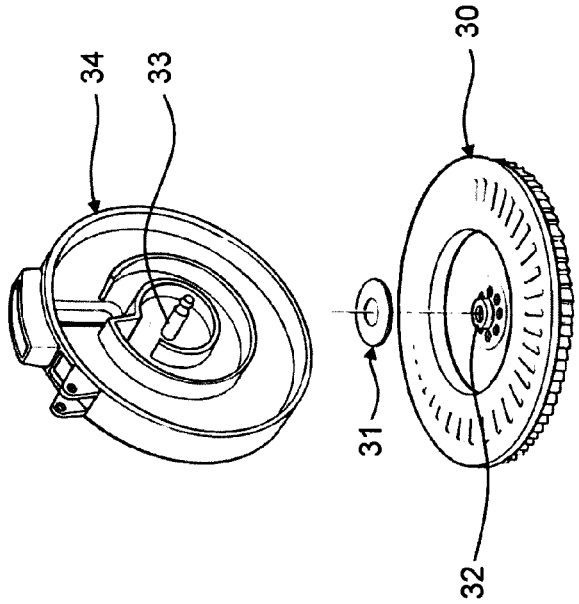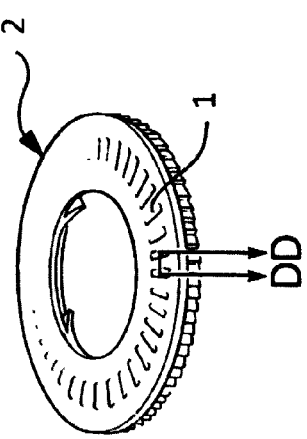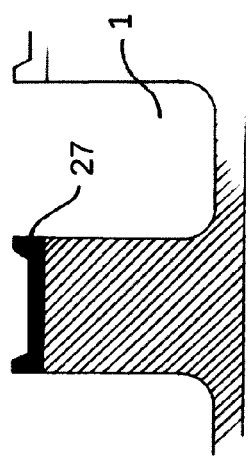
Fig 8B
Fig 8A
Fig 7A
Fig 7B
D-D

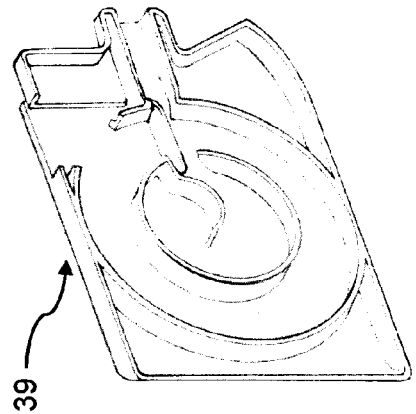
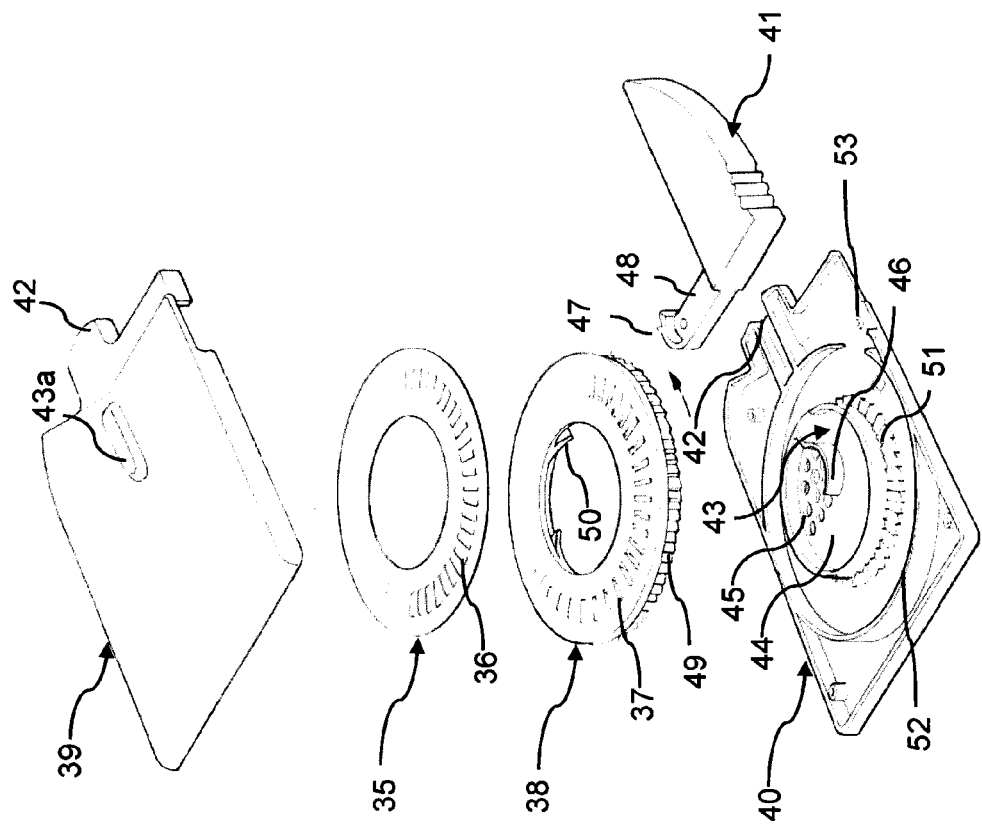

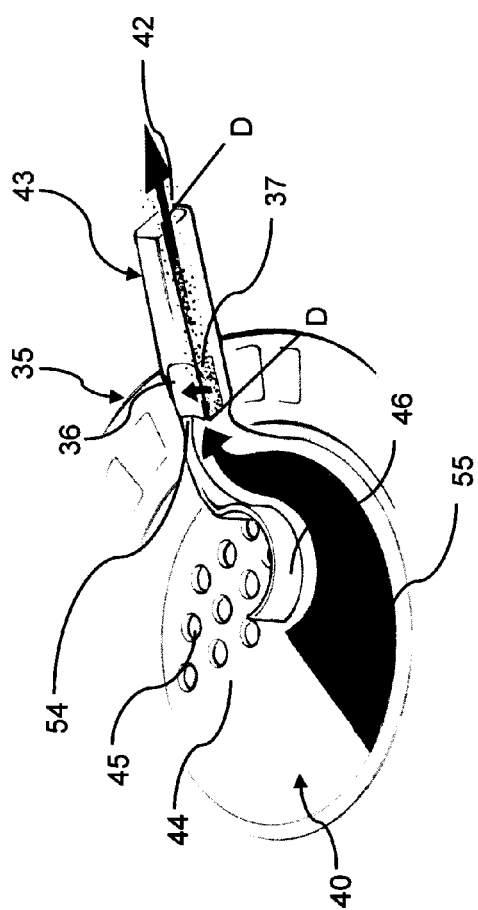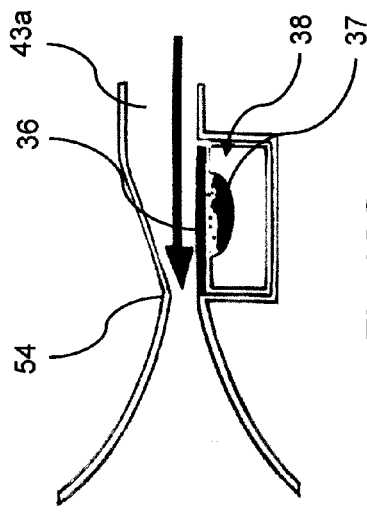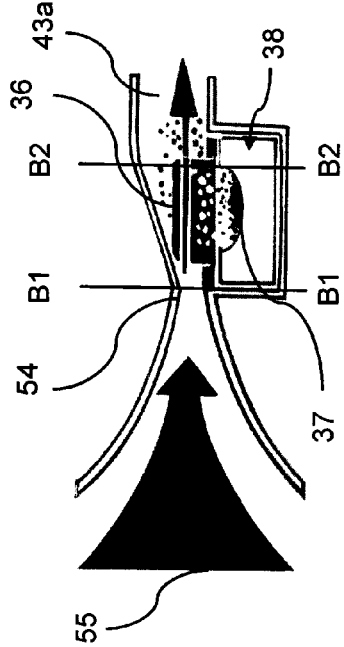

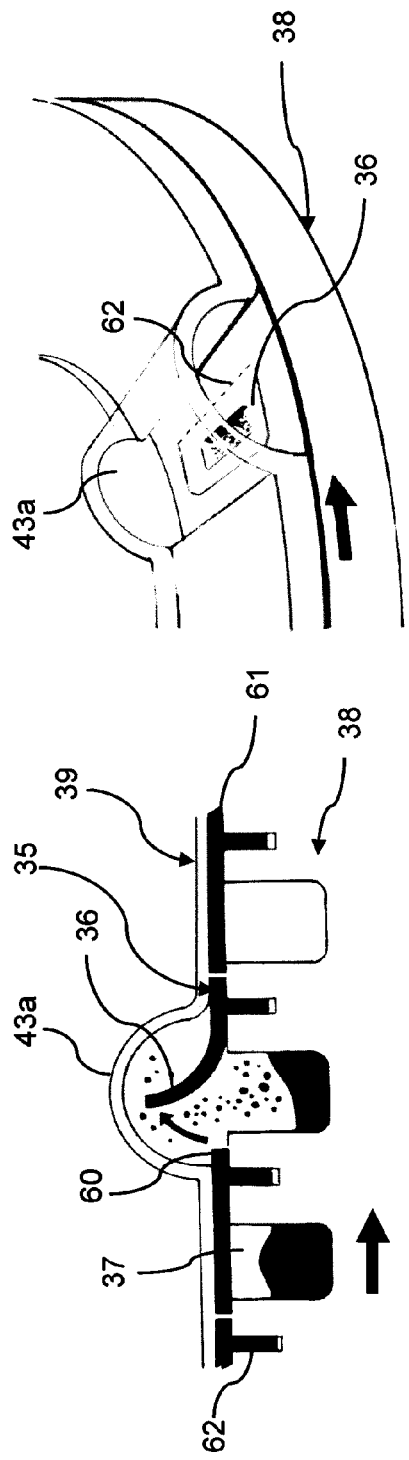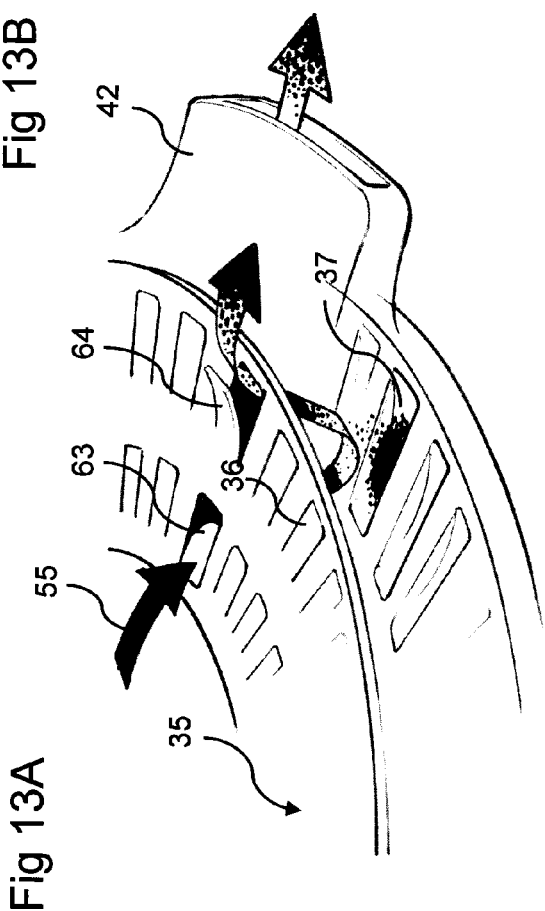

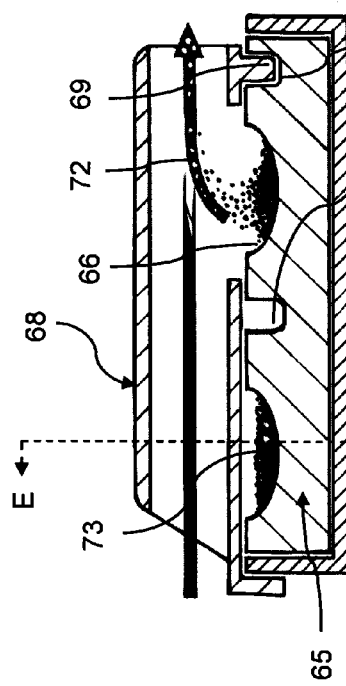
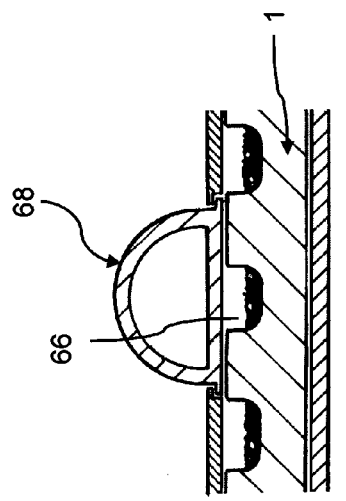
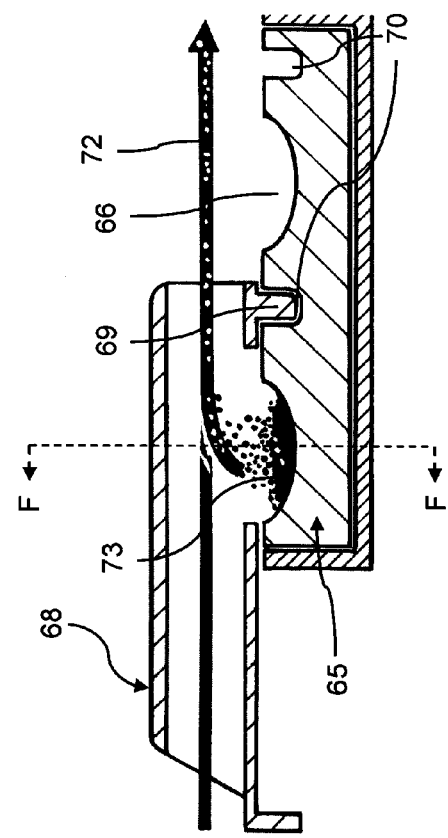
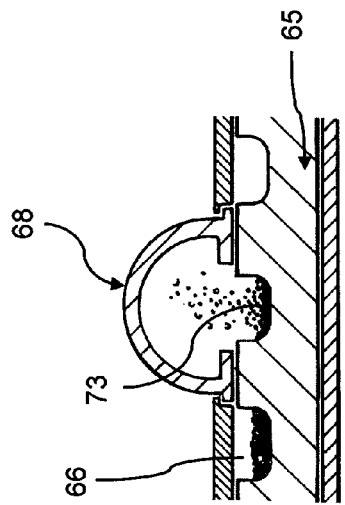

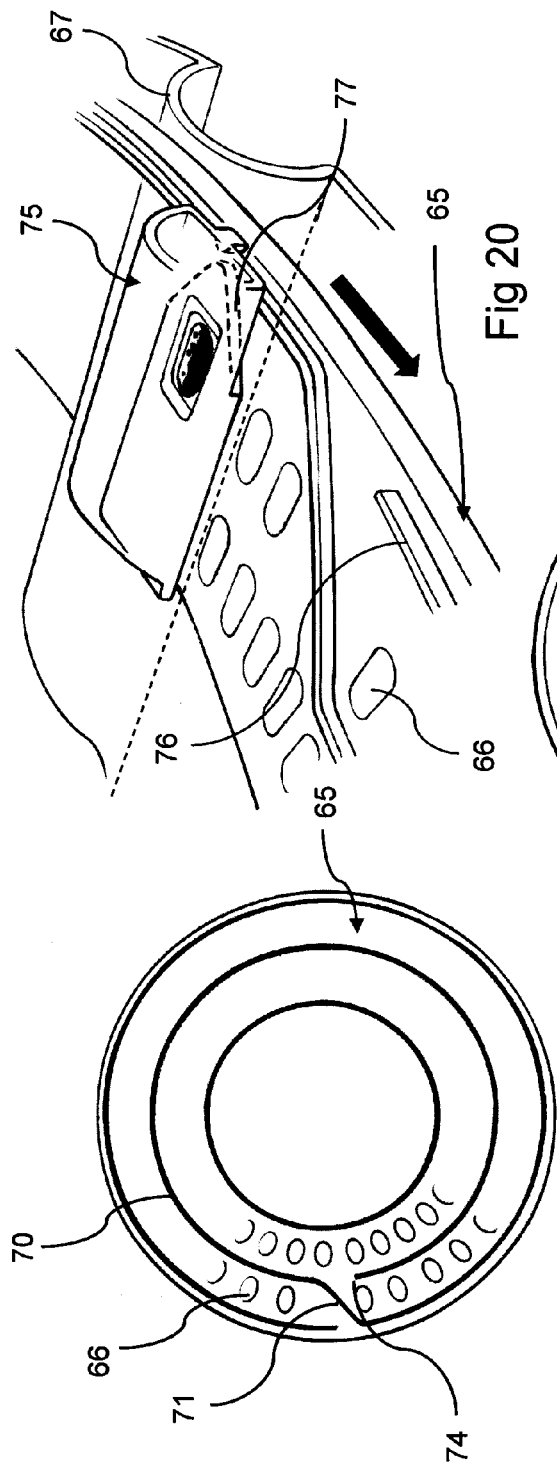

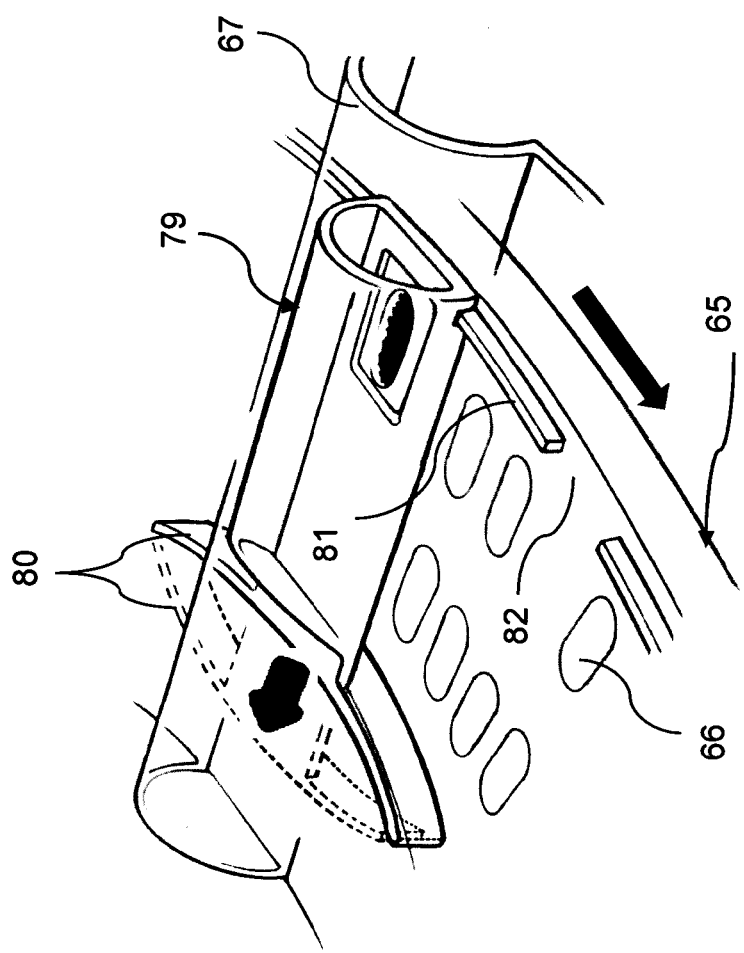
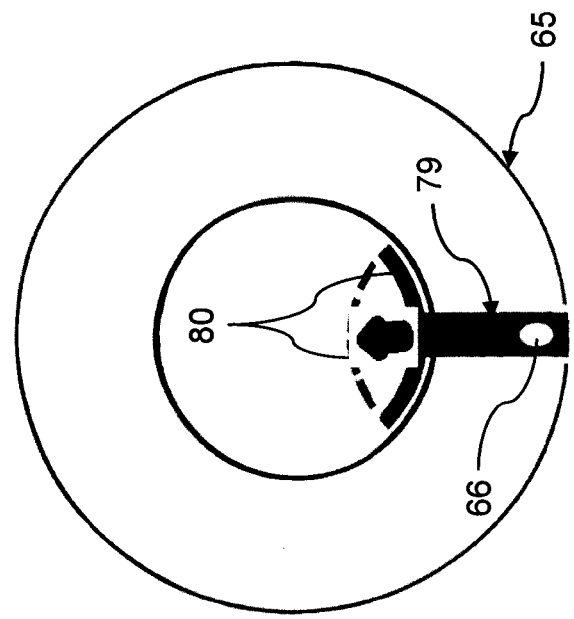
Fig 22A
Fig 22B

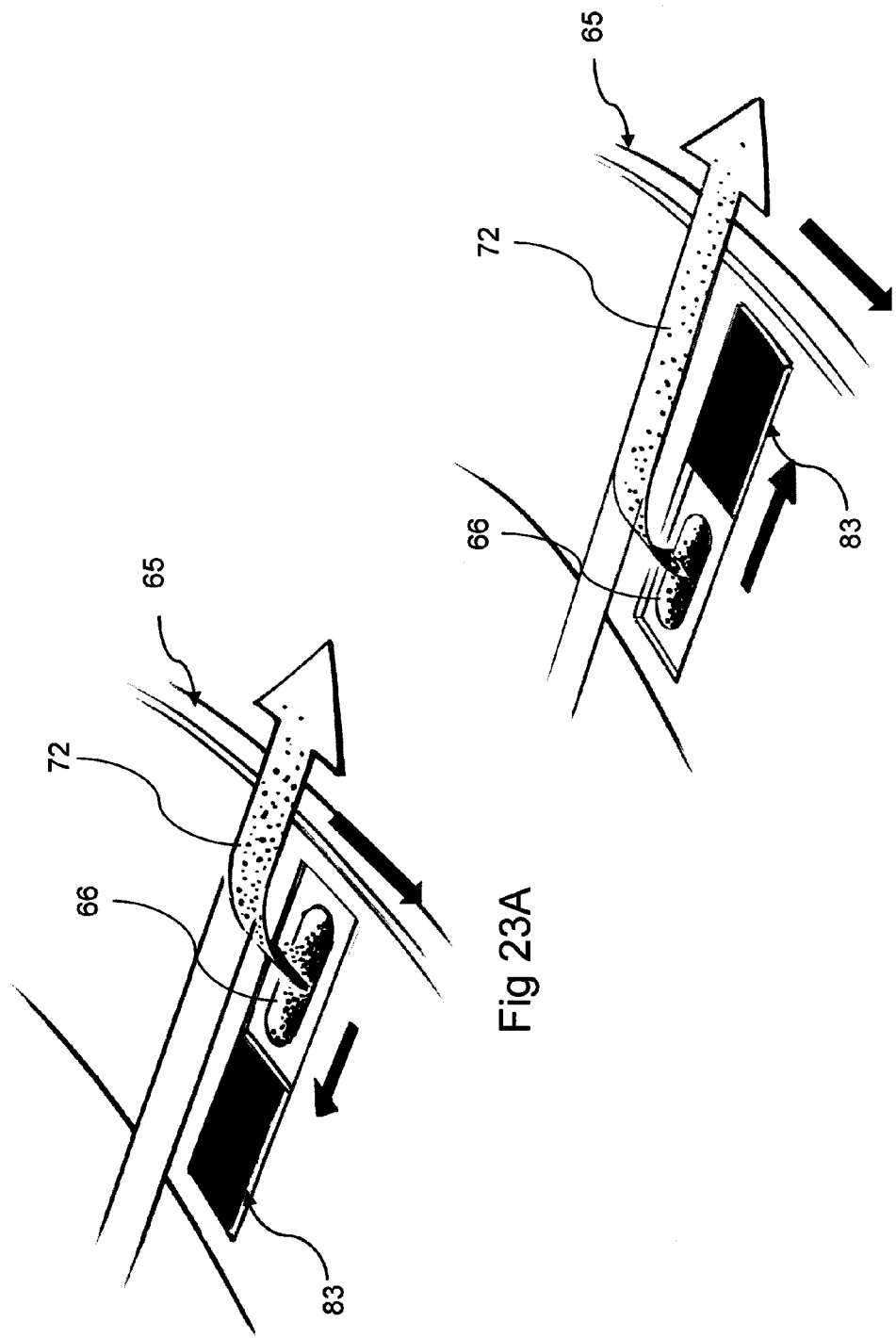

INHALATOR FOR SUBSTANCES IN POWDER FORM

PRIORITY CLAIM TO RELATED APPLICATIONS

This application is a U.S. National Stage application filed under 35 U.S.C. § 371 from international application serial number PCT/SE2012/000039, filed Mar. 21, 2012, and published as WO2012/128692 A1 on Sep. 27, 2012, which claims priority to Swedish Application No. 1130016-7, filed Mar. 21, 2011, and to Swedish Application No. 1130104-1, filed Oct. 26, 2011, and to Swedish Application No. 1130122-3, filed Dec. 18, 2011, which applications and publication are incorporated by reference as if reproduced herein and made a part hereof in their entirety, and the benefit of priority of each of which is claimed herein.

TECHNICAL AREA

The present invention relates generally to multidose inhalation devices for powdery substances. Specifically it refers to a so-called multidose-inhaler (DPI, Dry Powder Inhaler) that is powered by the user's own respirational ability. Multidose-inhalers are intended to alleviate illnesses caused by asthma and other ailments that prevent normal respiration.

TECHNOLOGY BACKGROUND

On the market today, there are a number of inhalers for powdery substances, most of which are so-called multidose—inhalers. Those currently marketed are relatively large and clumsy in their execution, which means that storing them in clothes/handbags and also the handling of them are not very user-friendly. Another problem is that they do not always deliver the precise and intentional dose and that unintentional feeding forward of new dos is possible—which means that the user, by mistake, may receive double or even larger dos. When the dose is loaded in position to be inhaled, the user can accidentally blow air into the multidose inhaler so that moisture can accumulate and cause the powdered substance to get stuck together. Further, the known multidose-inhalers, consists of many parts, making them complicated and thus expensive to manufacture and thus expensive to buy for the end user. A large number of components also increase the number of confounding factors. At a given quality level the number of possible errors, in principle, increases linearly with the number of parts. And it is desired that the inhaler contain many doses, for example, 60 doses or more, to increase comfort for the user.

There have been many attempts to construct multidose—inhalers that solve these problems. The following, inhalers U.S. Pat. No. 6,273,085, U.S. Pat. No. 7,275,538B2, U.S. Pat. No. 6,871,647, U.S. Pat. No. 7,395,821B2 and US2009205657A1 are examples of such attempts. A disadvantage is that they have at least nine or more parts and some form of closed encapsulation of the powdery substance to be inhaled. In order to expose the substance, the encapsulation must be pierced, a seal rolled up, torn of or similar in order to make the powdery substance free for inhalation. This encapsulation or rather, the mechanism needed to break the seal, is the crucial factor that requires a number of individual parts and makes the multidose-inhaler relatively large and unwieldy. These problems are solved by the present invention.

U.S. Pat. No. 6,273,085 discloses an inhaler with a separate powder cartridge. The cartridge comprises a disc having axial bores constituting the powder chamber. On the top and bottom there is a seal enclosing the holes in the disc and thus seals the powder chamber. An upper and lower spring washer creates the sealing pressure. Thus, five parts are used, only for the function to contain the powder chamber. In the present invention, two parts are used for the same function, the dose ring and the upper housing portion. In the present invention the upper housing portion constitutes one of the two parts to form an enclosed powder chamber. The present invention uses two parts compared to the prior known patent's five parts. The fewer parts gives lower manufacturing costs, lower assembly costs and fewer confounding factors.

U.S. Pat. No. 7,275,538B2 discloses an inhaler with powder chambers, in the shape of cylinders, which are placed one after another in a disk that uses a piercing device with a needle to penetrate one chamber at a time in order to expose the content of the chamber and thus make it possible to inhale its contents. Each chamber is advanced, one at a time, after which it is pierced from the inner part of the disk. The piercing arrangement means that the design height is approximately 11 times as high as the air channel's height. Powder can get stuck on the needle that penetrates through both Chambers, powder can also end up in the aerodynamic shadow under or behind the parts of the penetrated foil that folds inwards in the powder chamber when its penetrated, and the foil can also contaminate the powder. The solution hampers production because the chambers are to be filled with powder and then sealed on both the inner and the outer part of the disk. The numbers of parts are at least nine.

U.S. Pat. No. 6,871,647 describes a device that consists of three times as many parts as the present invention. In order to expose the dose that will be inhaled from the chambers, an encapsulation/tape needs to be "rolled up" or "peeled" off. This complicated method of opening the chambers also endangers that parts of the encapsulation material will be mixed with the substance in the powder chamber and thus contaminate it. The inhaler is considerably thicker and in every way bigger in volume and therefore more bulky in its design than the present invention and, therefore, more cumbersome to store and manage.

U.S. Pat. No. 7,395,821B2 discloses a device, which consists of twelve parts where the covering tape, which is arranged on the chambers with medicament, is to be pierced and then inhaled through the "needle" used for penetration. Contamination of the substance to be inhaled is therefore at risk and also that the powdery substance in the powder chamber, may end up in an "aerodynamic shadow" i.e. that not all of the available dose is inhaled since the powder can get caught on the needle that penetrated the sealed chamber and also end up outside of it, during inhalation. The feed forward of doses and the management of the inhaler at inhalation also requires that two hands are used. This is because the upper and lower parts needs to be rotated in opposite directions to forward a new dos and that a "pin" needs to be pressed in order to penetrate the covering sealing in which the substance to be inhaled is located. This inhaler too is considerably thicker and in every way bigger in volume and therefore more bulky in its design than the present invention and, therefore, more cumbersome to store and manage.

US2009205657A1 describes a device which contains twice as many parts as the present invention, as well as where the tape covering the powder chambers, must be drawn away, pierced, pulled apart ("blisters"), etc., to enable the user to inhale the powdery substance. Thus the design uses a completely different sealing solution than the present invention, resulting in the above-described risk of contamination. These sealing solutions also means that space has to be spent for the opening mechanism that is needed to expose the powder to be inhaled. That in turn means that the size of multidose-inhaler inevitably will become larger in size than the present invention, because the method that is used in the present invention, to expose the powdery substance, eliminates the necessity of such a mechanism. Even this famous inhaler is considerably thicker and larger in size, and therefore more bulky in its design than the present invention and, thus, more cumbersome to store and manage.

U.S. Pat. No. 7,571,724 discloses a design with two dosage rings, which are placed one over another. Here, the diameter—size becomes a problem when the number of doses increases, and also the inhaler thickness, which will make it difficult to use and impractical. This solution with two dosage rings superposed, provides a large and unwieldy inhaler.

WO2009102273 discloses a dose ring with containers with an opening arrangement, which is made to open each respective powder chamber. The solution refers mainly to the opening arrangement used to expose the doses of each powder chamber. An inhaler with the described arrangement will be considerably larger in size when the number of doses approaches or exceeds 60 doses.

U.S. Pat. No. 7,571,724 and WO2009102273 thus shows structures that use dose rings, but the dose rings does not hold a sufficient number of doses if the size or thickness of the inhaler shall be kept to a reasonable and user-friendly level. Prior art does not display any solution that demonstrate n inhaler with a dose ring that is small, flexible and easy to carry along, that will fit many doses and yet is inexpensive to produce.

SUMMARY OF THE INVENTION

The multidose Inhaler according to the invention consists of a dose ring containing powder chambers, in the form of depressions in the said dose ring, substantially oriented in a circle. The powdery substance is encased by the housing and the dose ring which seals against each other. The housing may tentatively be provided with a local elevation comprising an air channel. Where the protection of mouthpiece, which simultaneously serves as advancing mechanism, opens, the dose ring rotates on one step at a time and a powder chamber is fed to the position of the air channel and is thus exposed to the air flow caused by inhalation through the inhaler. It is then possible for the powdery substance to be carried/added to the airstream.

The seal between the dose ring and the housing can be made in different ways. One example is that the dose ring, by double injection moulding, is fitted with a soft surface layer which then seals against the housing. Another solution is, by double injection moulding, is fitted with a soft surface layer on the side that is pressed against the dose ring. A one way valve prevents the user from accidentally blowing air into the inhaler.

The purpose of the invention is to create a multidose-inhaler that is as thin as possible. The aim is to reduce the design height of multidose-inhaler so that it can conveniently be able stored, for example in a breast pocket. Length and width is reduced to about credit-card size, which means that the multidose-inhaler is significantly smaller than what is normal amongst known multidose—inhalers and that the thickness is only about one-third. The reduced design height is an important feature for the users. This can be obtained by designing the geometrical form so that the building height is approximately the sum of the wall thickness of the lower housing, the wall thickness of the base of the dose ring and height of the powder chamber and the wall thickness of the upper housing. This height applies to at least approximately 95% of the inhaler surface. This unique geometric shape gives clear advantages in that it allows for a significantly lower building height than the famous inhalers.

A further objective of the invention is to design it with as few parts as possible to facilitate production, thereby making the device more cost-effective to produce, which gives the end user a much cheaper alternative to a multidose inhaler than what is available on the market today. The parts consists mainly of an upper and a lower housing that encloses the dose ring, the advancing mechanism and the one way valve, a total of five components. Due to the few parts and the specific structure the multi-dose inhaler will be straightforward and cheap to assemble. Automation of production can be conducted using standardized picking robots since all components have the same mounting orientation. Thus there is no need for manual operations during manufacture.

Another purpose of the invention is that the handling of multidose Inhaler shall be as easy and user friendly as possible while at the same time minimizing possibilities of misuse. You can take it, for example, out of the breast pocket, put your thumb on the advancing mechanism, feed forward a dose, inhale, then close it and put it back into the breast pocket.

Thus, the design thus makes it possible for the user to manage the multidose inhaler using only one hand while, no matter how the user holds it, it ensures that the entire dose is inhaled. The device also eliminates the risk of, inadvertently; inhale a double dose at the completion of feeding forward and inhalation. After the doses are consumed the multidose inhaler is discarded or recycled.

In a variant, the powder chamber is opened by that the housing sealing effect, ceases at the air channel above said powder chamber. At each feeding forward of the dose ring, one powder chamber at a time is uncovered from its sealed enclosure, through the dose ring's sliding motion against the housing at the sealing surface. The powder chamber is rotated in this manner, in one direction towards the air channel, to be exposed when the feeding is complete. The solution eliminates the need for devices that punctures the foil, tears it open, lifting a rubber seal or lifting a sealing cap. Since the exposure of the powder chamber occurs in this unique way, the building height and the number of parts are reduced to a minimum while maintaining safety and good usability. The design also eliminates the risk of contamination of the powder and that parts of the medicament end up in aerodynamic shadow behind parts of the perforated enclosing foil.

The disclosed multi-dose Inhaler is thus substantially smaller and above all thinner than known multi-dose inhalers. The present invention comprises substantially fewer parts than known multi-dose inhalers, and does so without sacrificing safety and with a simpler handling. The inhaler will also, with the proposed design, be straightforward and hence inexpensive to manufacture.

An alternative embodiment is a multi-dose Inhaler comprising a dose ring containing powder chambers, in the form of depressions or recesses in said dose ring, substantially oriented in a circle. The dose ring abuts a sealing material in the form of a seal, which is arranged directly adjacent to said recesses. In the seal there are arranged openable element preferably dimensioned to three quarters of the area of each powder chamber. The openable elements are cut or pierced to form a flap in the seal. No material has been removed so that the movable element fits exactly into the surrounding sealing material, and the powdery substance cannot pass by or through the slit. The seal may, for example be glued or fixed to the dose ring through notches between the powder chambers in which corresponding elevations in the sealing ring fits. Only at one long side of the powder chamber is the seal snapped to the dose ring. The inhaler housing is pressing against the sealing of the powder chambers thus helping to hold the seal in place at the powder chambers. The housing can for example be provided with a local embossment at the air channel portion, wherein the sealing function between the housing, the seal ring and the dose ring ceases. When the protection of the mouthpiece, which simultaneously serves as advancing mechanism, is opened, the dose ring rotates one step and one powder chamber is thereby fed to the air channel and exposed to the air flow caused by inhalation through the inhaler. The air channel is formed so that an underpressure, a venturi effect, occurs in the region of the dose ring. A constriction is arranged upstream of the dosing ring and the powder chamber that will deliver a dose of powder. This restriction causes a speed increase of the air flow. After the restriction the air channel widens suddenly or gradually giving an underpressure. The widening is located in the area of the exposed powder chamber that will deliver a dose of powder. The underpressure lifts/opens the openable element and the air that flows by pulls the powder from the powder chamber.

Another alternative embodiment is a dose ring with two lines of Powder chambers. The aim is that with a given size of dose ring fit more powder chambers. It is desired that the inhaler contain many doses, for example, 60 doses or more, to increase comfort for the user. A market leading inhaler has 60 doses but do not use a dose ring as containers for the medical doses, but is constructed in a more complicated manner with a rolled-up blister band that forms the powder chambers and that is torn off when fed forward so that a dose at a time is exposed to an air flow when the user inhales. This inhaler has formed a pattern of the number of doses it is desirable to include in an inhaler. However, the solution involves a large number of parts that must be assembled which then adds to the cost of manufacturing the product. An inhaler with a dose ring as in the present invention can be manufactured with fewer parts, but the downside is that the number of doses contained in the inhaler will be fewer than 60 if not the inhaler is made in large format, but then it becomes impractical for the user. The powder chambers need to be of a minimum size to hold enough powder. A powder chamber size of 16-18 cubic millimeters is desirable or necessary depending on drug type. There is a partition wall separating the powder chambers from each other and it needs to be designed with a certain width in order to accomplish their task. Often, the wall thickness is at least 1 mm. This leads to that inhalers with dose rings usually contains about 30 doses. To increase the number of doses the diameter of the dose ring needs to be increased. Alternatively, two dose rings can be placed upon each other. It means however that the thickness of the inhaler becomes unwieldy. In the market for inhalers there are inhalers with diameters up to 85 mm. The user needs to take up and put back such inhalers in a handbag or similar as it becomes impractical to put it in your pocket. An inhaler that is greater than 85 mm would have a competitive disadvantage simply because of its size. The problem is to design an inhaler with a dose ring with 60 or more doses, without letting the diameter become too large, for example, exceed 85 mm or making the dose ring excessively complicated in composition and function.

The purpose of the invention is achieved with a dose ring as described in the present invention, with powder chambers provided in its surface. The powder chambers may be arranged for example in at least two substantially circular lines, an outer and an inner, or in a helical form in which each powder chamber is placed in a gradually changing distance from the centre of the dose ring. An uncovering device for example comprising of an air channel, is arranged to slide over the surface of the dose ring substantially radially and transversely to the rotation direction of the dose ring and thus expose one powder chamber at a time. When the air passes through the uncovering device can for example, an underpressure be created in the air channel portion, thereby lifting a sealing cap, alternatively can the intended device mechanically puncture or tear off a covering foil or in other ways break the sealing function which keeps the powder in the powder chamber. The air flow ensures that the powder dose follow the air flow out of the inhaler and down into the user's lungs. A seal may be disposed between the dosing ring and the adjacent surface of the rotationally fixed part. In the seal, the opening lids can be arranged. The uncovering device is preferably sliding in a, for the purpose, arranged guiding and/or air channel through which air can pass from an inlet of the inhaler to an outlet mouthpiece. The air moves when the user inhales. The mouthpiece is uncovered by the user before an inhalation.

The uncovering device is preferably first positioned over a powder chamber at the periphery of the dose ring. The position of the uncovering device is determined by a guide track provided in the surface of the dose ring. The uncovering device has a guiding pin adjusted for the guiding track, so that the uncovering device can follow the guide track when the dose ring rotates. When the inhaler is supplied to the user the dose ring is located so that no powder chamber is in a position to be inhaled. This has two purposes; the first dose is more moisture resistant since the uncovering device is open to the air channel, and, it creates the space for the changing point needed for the change of track position that changes the radial position of the uncovering device on the dose ring by that the guiding track is arranged to run from an outer position to an inner position nearer the centre of the dose ring. When the user has inhaled the last dose of the outer line and by a the subsequent inhalation feeds the dose ring to the next dose, the uncovering device guiding pin follows the guiding track shifting point to the inner line of powder chambers. This is conveniently performed in the dose ring surface at level with the start position where there is no powder chamber.

The guiding track is therefore arranged to position the uncovering device over the line of the powder chambers. The solution means that the uncovering device is first positioned over the outer line of the powder chambers, which can be emptied one by one. When the last powder chamber in the outer line is emptied and the users feeds forward for the next dose, the uncovering device follows the guiding track which is arranged with an slanted section to lead the uncovering device towards the centre of the dose ring, to be positioned, at the completion of the feed forward, over the first powder chamber in the inner line so that inhalation can be made for this dose. At each feed forward a new dose is transferred to the inhaling position, and the inner line of the powder chambers can be emptied one by one until all the doses has been inhaled.

In this way, at least, double lines with powder chambers can be arranged in the dose ring by using only one additional detail. Of course, it is possible to organize additional lines of powder chambers and guiding tracks in the dose ring. The dose ring can thus contain 60 doses or more while the inhalator consists of 6 parts instead of 5 parts, but it is still considerably fewer than the approximately 13 pieces plus tape with powder chambers which is required in known inhalers. The solution can, of course, alternatively, be so arranged so that the inner line of powder chambers is emptied first, rather than the outer.

An alternative solution is that the uncovering device position is determined by a cam arranged to stand up from the dose surface and for example has a constant radial position in the rotating direction of the dose ring. The uncovering device has in its bottom surface a, to the cam, customed guiding track, so that it can follow the cam when the dose ring rotates. The solution gives, for example, that the uncovering device is first positioned over the outer line of the powder chambers, which can be emptied one by one. When the last of the powder chambers in the outer line is emptied and the user feeds forward the next dose, the uncovering device follows the cam towards the center of the dose ring so that it is, once the feed forward procedure has been completed, is positioned over the first dose of the inner line, and inhalation of that dose can be performed. With every feeding forward a new dose is positioned at the place of discharge in the air channel and the inner line of powder chambers can be emptied one by one until all the doses have been inhaled.

Another optional solution is to let the uncovering device be loaded by a spring that can also be integrated into the uncovering device that is, e.g. crafted of the same plastic material as the uncovering device, or in any of the adjacent parts. The uncovering device according to the invention, is arranged to move/slide radially over the dose ring in an air channel arranged substantially transverse the dose ring Initially is the uncovering device positioned over the outer line of powder chambers. The integrated spring presses the uncovering device inwards towards the center of the dose ring and a cam blocks the movement, in its end position, towards the center of the dose ring. When the last powder chamber in the outer line has been emptied and the user feeds forward the next dose, the cam ceases and the uncovering device slides inward by the force of the spring and is positioned over the inner line of the powder chambers. The drift inwards may be limited by a cam or other suitable device in those parts, which prevents the uncovering device to glide longer than intended. The invention may, alternatively, be arranged so that the inner line is emptied first, rather than the outer.

The invention may also contain more than two lines of powder chambers. The spring must not necessarily be integrated, but can be a separate detail. However this means that another part is needed at manufacturing. The direction of the spring pressure can be reversed, that is, out towards the periphery of the dose ring instead of towards the center.

Yet another solution is that the powder chambers are arranged in helical form, instead of in a circle. Instead of two or more lines of powder chambers arranged in circles, is a single line of the powder chambers formed, but arranged in a helical form in the surface of the dose ring. The uncovering device can slide radially over the surface of the dose ring and follow the shape of the helical by using a guiding track arranged to control the radial position of the uncovering device. The guiding track is arranged in the corresponding helical form next to, for example, the outer side of the powder chambers, so that the uncovering device is always fed forward to and positioned over the powder chamber to be emptied.

Regardless of whether the powder chambers are arranged in a circle or in a helical, the chambers should be oriented in a radial line from the center of the dose ring out to the edge of the same, because the uncovering device has a constant width and is sliding radial inward or outward from the center of the dose ring. Once the dose ring has rotated one complete revolution the uncovering device shifts position and moves/slides inwards or outwards, depending on the preferred embodiment, at the same time as it covers the already emptied chamber while it exposes the inner or alternatively the outer chamber that still contains a dose.

In an alternative design of the guiding of the uncovering device, in the example with the arrangement of the powder chambers in helical form, it is designed with an integrated spring that presses the uncovering device against center of the dose ring. The cam that hinders movement will, for each dose have a changed/reduced radial position after each feed, so that the uncovering device is placed over the powder chamber that is to deliver its powder dose.

SHORT LIST OF DRAWINGS

The invention is described in more detail below in some of the preferred design examples with help of the appended drawings.

FIGS. 1A and 1B shows an exploded view of an inventive multidose inhaler.

FIGS. 2A, 2B and 2C shows an exploded view of an inventive multidose inhaler, and how the air flow carries the powdery substance via the air channel, out through mouth piece.

FIG. 3 shows an inventive multidose inhaler where the underside of the dose ring, with its numbering of the powder chambers is visualized.

FIGS. 4A, 4B and 4C shows an inventive multidose inhaler where the feed forward occurs during the first half of the advancing mechanism motion and how the advancing mechanism is linked to give access to the mouth piece.

FIGS. 5A and 5B shows an inventive variant of multidose inhaler where it is supplemented with a one-way valve mounted in the mouth piece.

FIGS. 6A, 6B, 7A and 7B showing inventive variants of the invention of the multidose inhaler where the position of the sealing layer is shown as well as variants of how the seal can be designed.

FIGS. 8A and 8B shows an alternative solution where the dose ring constitutes one of the housing bodies.

FIGS. 9A and 9B shows an exploded view of an inventive multidose inhaler.

FIGS. 10A, 10B and 10C shows an inventive multidose inhaler in an exploded view, and how the air flow carries the powdery substance via air channel out through the mouth piece, how the design of the air channel achieves to open the openable element by the use of underpressure.

Figure 11:
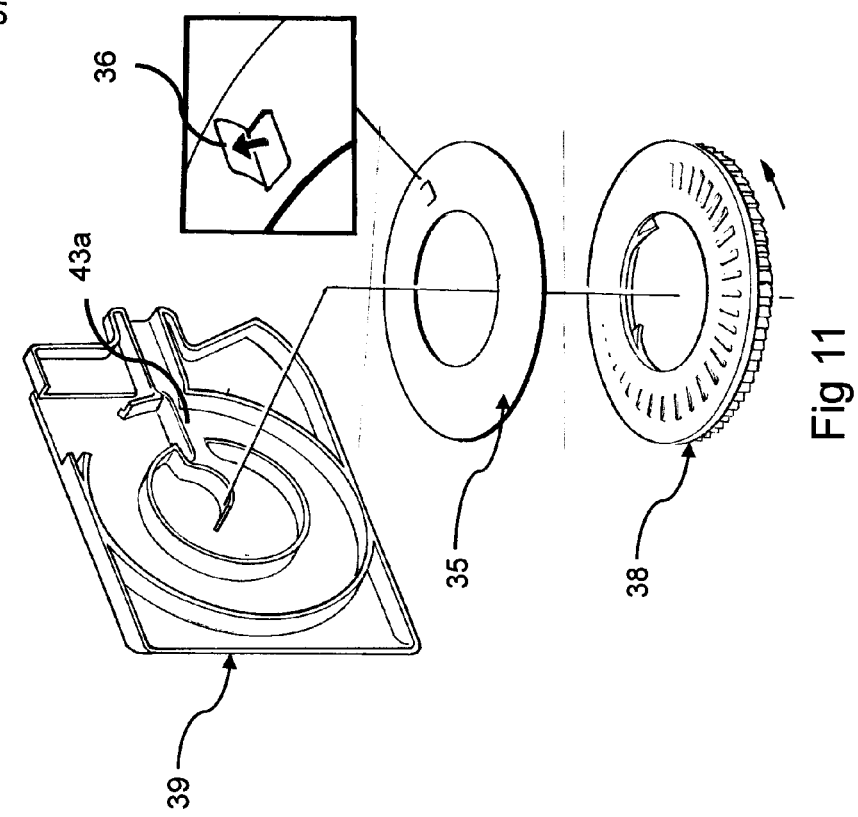

FIG. 11 displays an alternative design where the seal is attached to one of the housing bodies.

Figure 12:
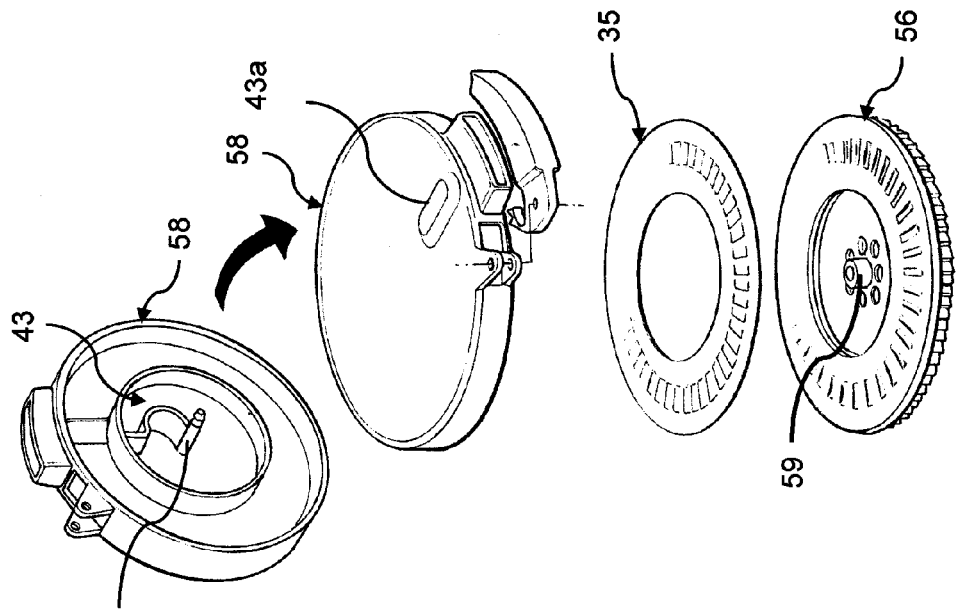

FIG. 12 shows, in an exploded view, an alternate design where the dose ring constitutes one of the housing bodies.

FIG. 13 shows an alternative design of the openable elements and the way they are attached.

FIG. 14 shows an alternative design of the openable elements of the seal, and where two openable elements, one for incoming air and one for the outbound air, are arranged.

Figure 15:
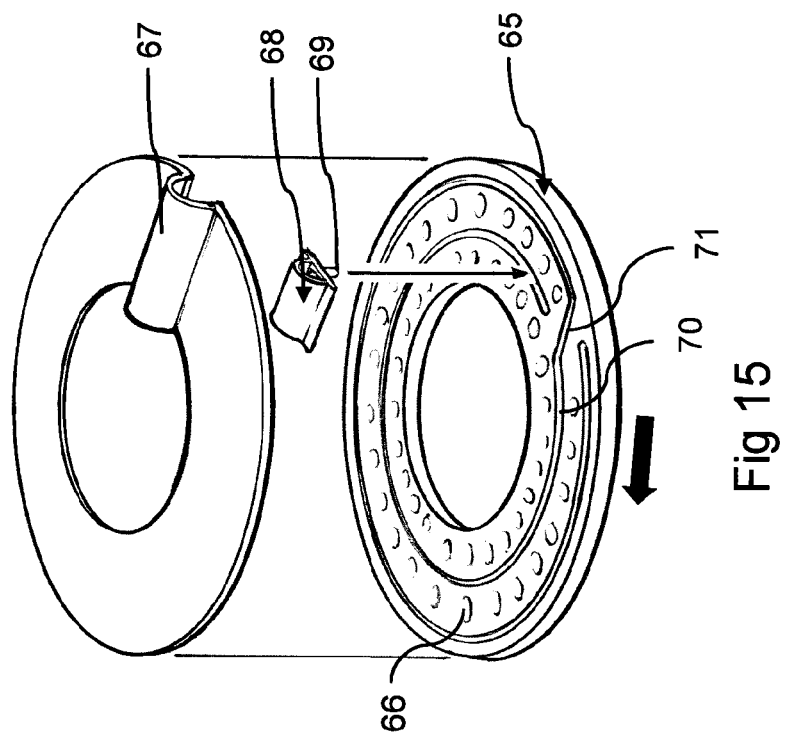

FIG. 15 shows a simple exploded view of an inventive dose ring with a rotationally fixed part with an uncovering device arranged in an air or guide channel.

Figure 16:
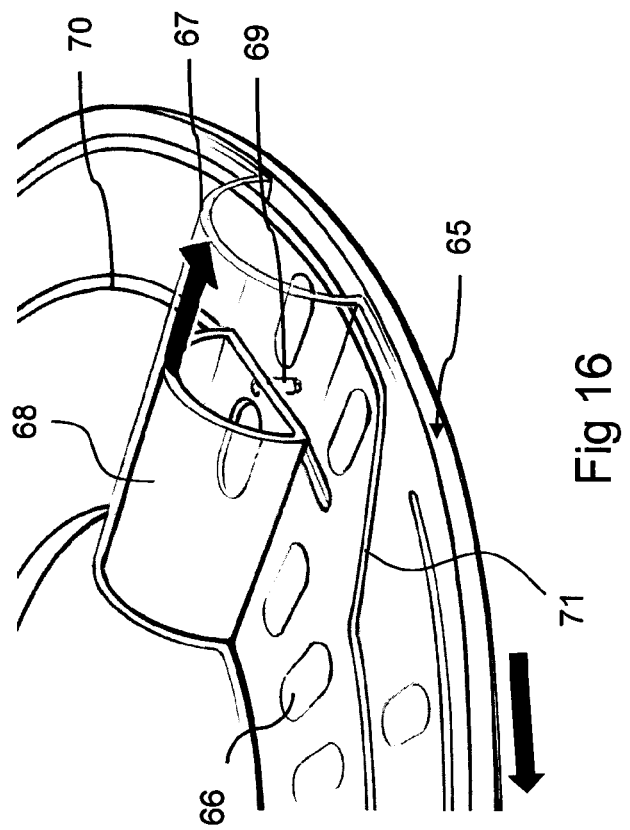

FIG. 16 is showing in more detail a view of the uncovering device in the air channel and where it displays how the uncovering device is guided by a guiding pin which runs in a guiding track made in the dose ring.

FIG. 17A displays a cross section of an inventive dose ring and where the uncovering device, in this situation, exposes the outer line of the powder chambers.

FIG. 17B shows a cross section of an inventive dose ring according to FIG. 17A where it s displayed how the uncovering device seals one of the powder chambers.

FIG. 18A shows a cross section of an inventive dose ring according to FIG. 17A but where the uncovering device in this position exposes the inner line of the powder chambers.

FIG. 18B shows a cross section of an inventive dose ring according to FIG. 18A where it is visualized how the uncovering device exposes one of the powder chambers.

FIG. 19 displays a view of an inventive dose ring with a number of powder chambers, about 60, and with a guiding track.

FIG. 20 shows, in more detail, a view of an alternative solution of the uncovering device where the guiding track has been replaced with a cam that stands up from the surface of the dose ring.

FIG. 21 shows an alternative design where the powder chambers are placed in the dose ring in helical form.

FIG. 22A shows, more detail I a view of an alternative solution in which the uncovering device runs against a cam arranged in the dose ring and where the movement between two different radial positions over the dose ring is caused by an opening in the cam and a spring which pushes the uncovering device towards the center of the dose ring.

FIG. 22B shows schematic and from above, the two positions of the spring, before and after the changing point.

FIG. 23A shows an alternative design of the uncovering device in form of a lid which can slide radially over the dose ring and that this is positioned for emptying the powder chambers in the outer line of the dose ring.

FIG. 23B shows the lid positioned for emptying the inner line of the powder chambers in the dose ring.

DESCRIPTION OF PREFERRED DESIGNS

FIG. 1A, displays a multidose inhaler consisting of a number of cavities, which will be named powder chambers 1 from this point forward, each containing a preloaded amount of powdery substance. The powder chambers 1 are oriented in a circular shape in a dose ring 2. The dose ring 2 is in turn enclosed between a rotationally fixed upper housing 3 and a rotationally fixed lower housing 4. The openings of the powder chambers 1 are arranged towards the containing upper housing 3. The multidose inhaler is equipped with an advancing mechanism 5, which, at the same time serves as a cover for the mouthpiece 6 opens also feeds one powder chamber 1 at a time, to a position for inhalation. In the inlet end of the air channel 7 is arranged in the lower housing, arranged inlet 8. The inlet consists of at least one, but preferably several, air holes 9, which are covered by a one way valve 10. The one way valve 10 prevents air from being blown into the multidose inhaler at the same time as it opens and enables inhalation. The air channel 7 downstream of the 10 one way valve is designed as a spiral 11 in order to catch powder that may fall from the powder chamber 1 and down into the air channel 7. This ensures that the powder is caught by the spiral 11 before it reaches the entrance 8. This solution means that the dose of medication/powder will assuredly be inhaled no matter how the multidose inhaler is oriented by the user during use.

FIG. 1A also shows that the advancing mechanism 5 consists of a cogged 12 advancing arm 13. When opening the advancing arm 13 advances the cog ring 14 in the dose ring 2 so that the next dose is fed forward in line with air channel 7 where the upper housing 3 has a local elevation that lies directly transverse the rotational direction of the dose ring 2. The length of the elevation and its width is slightly larger than the powder chamber 1, in order to ensure that the whole content of the powder chamber 1 is exposed. In the local elevation, which is a part of the air channel 7, thus there, the containment of the fed forward powder chamber 1 ceases. Thus when feeding forward one powder chamber is released from its containment towards the upper housing 3 and is exposed to/in the air channel 7. When inhaling through the mouthpiece 6 the powder chamber 1 is exposed to flowing air and the powdery substance can be drawn in, with the inhaled air. After inhalation, when the user closes the advancing mechanism 5, the advancing arm 13 springs away from the cogs in the cog ring 14 in the dose ring 2 on its way back to the starting position. Back stops 15 integrated in the dose ring 2 prevents the dose ring 2 from rotating backwards, by gripping the cogs in the lower housing cog ring 16 which is integrated in the lower housing 4. The cog ring 14 in the dose ring 2 along together with the back stops 15 and the lower housing cog ring 16, ensures thus that only one powder chamber 1 at a time can be fed into inhalation position. The backstops 15 are designed to give a leeway so that they can, when fed forward, spring up, over the cogs in the lower housing cog ring 16. This solution means that only one powder chamber 1 at a time can be placed in line with and exposed to the air channel 7.

FIG. 1B shows the underside of the upper housing 3. The sealing of the substance in the powder chambers 1 is fixed in height and can be found in the contact surface 17 between the dose ring 2 and the upper housing 3.

FIG. 1A also shows that, in the lower housing 4, there is localization 18 for the does ring 2. In the lower housing is also an axis 19 for the anchoring of the advancing mechanism 5 as well as an integrated lower housing cog ring 16 for the back stops 15 in the dose ring 2. At assembly is first, for example, the lower housing 4 placed in a measuring fixture. The dose ring 2, the one way valve 10 and the advancing mechanism 5 are then assembled in this part. After that the powdery substance is filled to the dose ring powder chambers 1. In the last assembly step the multidose inhaler is sealed with the upper housing 3.

FIG. 2A shows the air channel's 7 design and placement. It has its beginning at the one way valve 10 in the inlet 8, goes through the spiral 11, up over the fed forward powder chamber 1 and ends in the mouthpiece 6. The figure also shows that when a user makes an inhalation through the mouthpiece 6 an under pressure is created in the air channel 7 which causes the one way valve 10 to open for incoming air through the holes 9 in the lower housing 4, and the air flow passes through the spiral 11, passes over the exposed powder chamber 1 and pulls the powdery substance through the mouthpiece 6 down in user's throat. Furthermore, the air channel 7 is designed in such a way that no pockets with aerodynamic shadow are created, where the powder can get caught during inhalation. The design ensures that the user receives a complete dose at every inhalation.

FIG. 2B displays a cross section, A-A, through the upper and lower housings 3, 4 including the intermediate positioned dose ring 2. The intersection indicates the position where the upper housing 3 is pressed towards the dose-ring 2 and seals the powder chamber 1. This applies to all powder chambers 1 except one that is in line with the air channel 7 and is in discharge position.

FIG. 2C shows a cross section, B-B, through the upper and lower housings 3, 4 including the intermediate positioned dose ring 2. Section B-B is through the air channel 7 and the powder chamber 1 that is, in this position, exposed to the passing air flow 20.

FIG. 3 shows that the powder chambers 1 are arranged with numbers 21. The numbers 21 are located on the underside of dose ring 2, on the opposite side of the powder chambers 1. They are visible through a window 22 in the lower housing 4. The window 22 may be given for enlarging properties to facilitate reading. Through the window 22, the user can determine how many doses have been used, or if you like, how many doses that remain.

FIGS. 4A, 4B and 4C displays how the multidose inhaler is opened and how, when this is done, the dose ring 2 is fed forward and how the mouthpiece 6 then is made available.

FIG. 4B shows how the feed forward of a new dose occurs in the first half 23 of the advancing mechanisms 5 movement. During the first half of the advancing mechanisms 5 movement the cogs 12 on the advancing arm interlocks with the cog ring 14 in the dose ring. When half of the movement has been made, the advancing arm no longer interlocks with the with the cog ring 14 in the dose ring, and the winding of dose ring 2 ends. The mouthpiece 6 is not available for the user's lips until after more than half 23 of the total movement have been completed. In this way, it is assured that the dose of powder will be fully advanced before inhalation can occur.

FIG. 4C shows the multidose inhaler in the fully opened position.

FIG. 5A displays an alternative design where the multidose inhaler is supplemented with a one-way valve 24 placed between the mouthpiece 6 and the dose ring 2. In the lower housing 4 is an anchor point 25 of the said one-way valve 24, in the upper housing 3 in this alternative solution, is the corresponding anchor point 26 of the same valve shown in FIG. 5B. The complementarity one-way valve enhances moisture protection by making the exhaling of air into the air channel impossible. The one-way valve also ensures that the dose cannot fall out of the mouthpiece if multidose inhaler is held upside down when feeding forward a new dose. In this variant we therefore find, in addition to all the parts already described above, a one-way valve 24 with associated locations, 25 and 26 on the outlet side, i.e. in the mouthpiece 6.

FIG. 6A displays a seal 27 which is arranged in the upper housing 3. This sealing 27 may, for example, be achieved by double injection molding that is provided with a soft surface. The seal 27 could also be a separate part placed in upper housing 3 at the assembly of the device. The seal 27 is equipped with an evisceration or opening 28 located adjacent to the air channel 7. When activating the advance mechanism 5 the dose ring 2 rotates against the fixed upper housing 3, as indicated in the figure. When a powder chamber 1 is fed to the air channel 7, it is exposed in an elevation in the upper housing 3 that is arranged directly transverse the rotational direction of the dose ring 2. It is also conceivable that the air channel 7 is designed in the actual housing material of the upper housing 3 without extending beyond the upper housings 3 main external surface and not by making an elevation in the upper housing 3.

The cross section C-C in FIG. 6B, displays an alternative where the seal is designed to be integrated into the upper housing 3.

FIGS. 7A and 7B displays an alternative seal 29 that is integrated into dose ring 2 instead, and that, by double injection molding, is given a soft sealing surface.

FIGS. 8A and 8B displays an alternative design where the lower housing is eliminated and the dose ring 30 itself is part of the casing. The dose ring 30 has the same execution as described earlier. The advancing mechanism has the same design when it comes to its geometry, in relation to the dose ring 30. However, the design of the safeguard needs to be adapted to the essentially circular shape of the inhaler. The air channel in its entirety with the one way valve has the same shape as before. The one way valve 31 needs a slightly larger hole in the center to fit around the hole 32 in bottom of the dose ring 30. A shaft 33, which ends with a clips-feature, is located in the center of the upper housing 34. The shaft 33 extends towards and meets with a hole 32 in the center of dos ring 30. The hole 32 is designed with an opposite shape for the clips-feature located in the tip of the shaft 33 from the upper housing 34. When the dose ring 30 and the upper housing 34 is put together the shaft clips-feature engages the hole 32 in the dose ring, and creates a sealing pressure between the two components.

In an alternative design, the previously described one way valves 10 and 24 are eliminated or can possibly be retained as a complement in an inventive multidose inhaler which is broadly similar to the already described variant. In this variant, which description begins in FIG. 9A the proposed integrated seals 27 and 29 are replaced with a separate seal 35 with pre-pierced openable elements 36.

FIG. 9A shows an inventive multidose-inhaler consisting of a number of powder chambers 37 arranged in a dose ring 38, oriented in the circular shape, each containing a preloaded amount of powdery substance. The dose ring 38 is in turn arranged between a rotationally fixed upper housing 39 and a lower rotationally fixed housing 40. The powder chambers 37, has their openings oriented against the rotationally fixed upper housing 39. The multidose inhaler is equipped with a advancing mechanism 41, including a covering cap which, while it exposes the mouth piece 42 also feeds forward the dose ring 38 one powder chamber 37 at a time to inhalation position in the air channel 43. In the lower rotationally fixed housing 40 is arranged an air inlet 44 for the air channel 43. The air inlet 44 consists of one or more air holes 45. Downstream the air holes 45, after the inlet 44, is a spiral 46 designed, aiming at, as an extra safety measure, capture powder that could fall from one of powder chambers 37 if the user, for example, shakes the inhaler and/or if it is kept in a vertical position after a feed forward. This ensures that the powder is caught before it passes through the air holes 45. This solution means that the substance that the dose consists of, with certainty, will be inhaled as a whole no matter how the multidose inhaler is oriented or handled by the user, during inhalation.

A seal 35 is also arranged with pre-pierced openable elements 36 and the seal 35 can be arranged against the dose ring 2 where the openable elements 36 fit against a powder chamber 1 in dose ring 2. Appropriate material of the seal 35 can be, but not necessarily, EPDM (ethylene rubber diene monomer) which can be form sprayed in very thin layers.

The figure also displays that the advancing mechanism 41 consists of an advancing arm 48 which has cogs 47. When opening the inhaler the advancing arm 48 drives the dose ring forward, through that the cogs 47 on the arm grabs on to the ring of cogs 49 on the dose ring, so the next powder chamber 37 is fed forward to air channel section 43a of the air channel which is designed to be lined directly transverse the rotation direction of the dose ring 38. The inner length and width of air channel section 43a of the air channel are preferably slightly larger than the opening area of the powder chamber 37 in order to ensure that the entire powder chamber 37 is exposed in air channel section 43a. It is also conceivable that section 43a of the air channel is designed in the actual housing material of the upper housing 39 without extending beyond the upper housings 39 main external surface and not by making an elevation in the upper housing 39.

At air channel section 43a the fed forward powder chamber 37 is thus exposed and only the seal 35 with its pre fitted openable elements 36 is at this point covering the powder chamber 37. When feeding forward one powder chamber 37 at a time is then exposed from its sealed position against the rotationally fixed upper housing 39 and exposed in the air channel section 43a.

After inhalation, when the user closes the advancing mechanism 41, the advancing arm 48 springs away from the cogs in the cog ring 49 in the dose ring 38 on its way back to the starting position. Backstops 50 integrated in the dose ring 38 prevents the dose ring 38 from rotating backwards, by taking hold of the cogs in the cog ring 49 which is integrated in the lower housing 40. The cog ring 49 in the dose ring 38, along with the backstops 50 and the, in the lower housing, integrated cog ring 51, ensures thus, that only one powder chamber 37 at a time can be fed into position for inhalation. The backstops 50 are designed to give a leeway so that they can, at feed forward, spring up, over the cogs in the, in the lower housing 40, integrated cog ring 51. This solution means that only one powder chamber 37 at a time can be placed in line with and exposed to the air channel section 43a.

FIG. 9A also shows that there is, in the lower housing 40, a circular shaped edge wall 52 which keeps the dose ring 38 in position. In the lower housing 40 is also guiding hole 53 for the advancing mechanism. At assembly of the inhaler, first the lower housing 40 is placed in a measuring fixture (not displayed). The dose ring 38 and the advancing mechanism 41 are then assembled in this part. After that the powdery substance is filled to the dose ring powder chambers 37. The seal 35 is then assembled against the dose ring 38. In the last assembly step the multidose inhaler is sealed with the upper housing 39.

FIG. 9B shows the underside of the upper housing 39.

FIG. 10A Displays, in an exploded view, air channels 43 design and placement. It has its beginning at the air holes 45 at the air inlet, 44, and then goes through the spiral 46, up over the fed forward powder chamber 37 placed in the air channel section 43a and then ends in the mouthpiece 42. The figure shows that at inhalation through the mouthpiece 42 the fed forward powder chamber 37 is exposed to the streaming air. Air is taken in through the holes, 45, in the lower housing 40 after which it flows through the spiral 46. After the spiral, just before the air channel section 43a, in the air flow direction, is a constriction 54 arranged whereby the air speed increases at inhalation. In the area over the powder chamber 37, the air channel section 43a gradually widens resulting in an underpressure that lifts the openable element 36 in the seal 35 and the airflow pulls the powder from the powder chamber 37. The local underpressure is caused by a so-called venturi effect. The openable element 36 in the seal 35 resembles a flap or a lid. Thus, the powder is exposed to the airflow 55 and is pulled out of the inhaler along with inhaled air, through the mouthpiece 42, down into the user's throat. Furthermore, the air channel 43 is designed in such a way that no pockets with aerodynamic shadow are created, where the powder can get caught during inhalation. This design, together with the spiral 46 and the overpressure that is created through exhalation through the mouthpiece, and the covering openable element 36, ensures that the user receives a complete dose at every inhalation.

FIG. 10B displays a cross section D-D through the upper and the lower housing with the intermediate dose ring 38 and seal 35 and it visualizes the air channel section 43a and the powder chamber 37 that has been exposed in the air channel section 43a. In the figure it is illustrated how the air channel section 43a, at B1, tapers to provide a speed increase of the airflow. After B1 the air channel section 43a widens up to B2, which creates an underpressure in the range B1 to B2, over dose ring 38, which opens the openable element 36 in the seal 35.

FIG. 10C visualizes, using the same cross section D-D, what happens if the user happens to exhale into the mouthpiece 42 instead of inhaling. This creates instead an overpressure in air channel section 43a that closes the openable element 36 in the seal 35 at the exposed powder chamber 37. This effect prevents the powder from to be blown back, down the spiral 46 at the same time as it also protects the powder from the moisture in the exhaled air of the user.

The design of how the number of remaining doses are displayed, and the opening mechanism is in the above described variant, identical to that already described functionality in FIGS. 3 and 4A, B and C.

FIG. 11 displays another design on the already described variant, where the seal is 35 is arranged to be placed adjacent to the upper housing 39. The seal is 35 this is arranged to be rotationally fixed together with the upper housing 39 and is then arranged by a single openable element 36 placed in the air channel section 43a.

FIG. 12 displays an alternative design where a lower hosing is no longer needed and where instead the dose ring 56 itself constitutes the outer housing. The dose ring 56 has otherwise the corresponding design as described earlier. The advancing mechanism 41 also has the same design when it comes to its geometry in relation to dose ring 56. However, the design of the protective cap needs to be adapted to the inhalers essentially circular shape. The air channel 43 in its entirety, has the same design as before. A shaft 57 that at its end is fitted with a clips-feature is located at the center of the upper housing 58. The dose ring 56 is prepared with a hole 59 and when the dose ring 56 and the upper housing 58 is sealed together, the shafts 57 clips-function attaches itself to the hole 59 in the dos ring and creates a pressure between the seal 35, the upper housing 58 and the dose ring 56.

FIG. 13A displays how the cut surface of the openable elements 36 can be made straight 60 alternatively askew 61 cut surface in the seal 35. An askew cut surface allows the airflow to more easily open up the openable elements 36 partly by the fact that the friction between the openable elements 36 and the surrounding sealing material is reduced but also by that the air can more easily get hold of an askew cut surface 61. If the user exhales into the mouthpiece an overpressure is created in the air channel section 43a, the askew 61 cut surface contributes to that the openable element 36 is pressed down on the powder chamber 37 thus preventing the powder in the chamber from being exposed.

Furthermore, the FIGS. 13A and B and also shows that the seal 35 has been prepared with attachment means 62 so that the openable elements 36 are aligned on the side of the powder chamber 37 that is located in dose ring 38 rotational direction. This prevents the openable elements 36 from ending up in the wrong position under the upper housing 39 when the next dose is fed forward and positioned for inhalation in the air channel section 43*a*.

FIG. 14 shows an alternative design for the openable elements 36 in the seal 35. The seal 35 has, in the position over the powder chambers 37, two openable elements 63 and 64 for every powder chamber 37. One, at the inner part of the seal 35 closest to the center of dose ring 38 and the other in the outer part towards the mouthpiece 42. The airflow 55 is guided d down into the powder chamber 37 through the inner opening element 63 and out through the outer 64. FIG. 14 shows an example of how these openable elements 63 and 64 can be constructed. Several other designs with two openable elements 63 and 64 are also possible.

The dose ring of an inhaler such as the present invention can be designed in alternative ways so that more powder chambers can be fitted without increasing the diameter of the dose ring.

FIG. 15 shows an exploded view of an inventive dose ring 65 which, on one of its surfaces, is equipped with numerous depressions or powder chambers 66, containing a preloaded amount of substance, e.g. a medicinal product in powder form. The powder chambers can be oriented in at least two mainly circular lines, one external and one internal. An air channel 67 is arranged transverse the rotational direction of the dose ring and spans the powder chambers, which at the particular moment, in position for the emptying of the powder or the product. An uncovering device 68 is arranged to glide in the air channel 67 in radial direction over dose ring 65 and transverse its rotational direction. The uncovering device 68 in its radial alignment, determines which of the two or more, in line, positioned, powder chambers 66 that can be emptied of its content of medicines. The uncovering device 68 is equipped with a guiding pin 69 that is arranged to fit and follow the guiding track 70. The guiding track 70 runs, preferably circular, in the dose ring 65, outside the outer line of powder chambers where the outer line of the powder chambers are the first to be emptied, when the user uses the inhaler, one powder chamber 66 at a time. When the user has inhaled the last dose of the outer line, and for the subsequent inhalation occasion, feeds forward the next dose, the uncovering device 68 guiding pin 69 follows the guiding track 70 obliquely positioned toggle point 71, to the inner line of powder chambers. The guiding track 70 is thus, at the toggle point 71 arranged obliquely against dose ring 65 center and the guiding pin 69, and thus the uncovering device 68, follows the guiding track 70 and positions uncovering device 68 above the inner line of powder chambers 65 which then can be emptied one by one.

FIG. 16 shows a more detailed view of the above described design for FIG. 15. In FIG. 16 is the air channel and the uncovering device 68 attached to the guiding track 70 in the dose ring 65.

FIG. 17A shows a cross-section through dose ring 65, the air channel and an uncovering device 68. The uncovering device 68 guiding pin 69 is positioned in and runs in the steering track 70 which positions the uncovering device 68 opening on the outer line of the powder chambers 66. The airflow 72 passes over the exposed outer powder chamber 66 and pulls with it the powdery substance.

FIG. 17B shows a cross section E-E where the uncovering device 68 covers or seals inner row of powder chambers 66 in the dose ring 65.

FIG. 18A displays a cross section of an inventive dose ring in the same way as in FIG. 17A but where the uncovering device 68 in this position, exposes the dose of powder 73 in the internal line of powder chambers 66.

FIG. 18B displays a cross section F-F of the dose ring in the same way as in FIG. 18A where it is shown how the uncovering device 68 exposes one of the powder chambers 66 so that the dose of powder 73 can follow with the airflow.

FIG. 19 shows a view from above of the space efficiency of dos ring. A large number of, for example about 60 powder chambers 66 are here arranged in two lines in the dose ring 65. The guiding track 70 is arranged in dose ring upper surface and has a starting point 74 constituting the position of the uncovering device before first use. The guiding track 70 has an essentially circular shape with a toggle point 71 and is partially positioned next to/outside the outer line of powder chambers 66, and after the toggle point 71 next to/outside the inner line of powder chambers, i.e. between the two lines of powder chambers 66.

FIG. 20 shows in more detail a view of an alternative design of the uncovering device 75 where the guiding track has been replaced with a cam 76 that extends up from the surface of the dose ring 65. The uncovering device 75 is designed with an evisceration 77 which is arranged to follow the cam 76 and thus controls the radial position of the uncovering device 75 over the dose ring 65.

FIG. 21 displays an alternative variant where the powder chambers 66 are located adjacent to each other in the dose ring 65 in one long line, in helical form. It is thus important that the powder chambers 66 which are positioned inside one another, are arranged in line with each other in the radial direction from the center and out to the edge of dose ring 65 so that the uncovering device (not shown) with certainty can expose the entire powder chamber 66 after a feed forward. At each feed-forward the dose ring 65 gradually rotates a certain predetermined number of degrees. The uncovering device (not shown), thus gradually moves in radial direction on the dose ring 65 subsequently, at each feed forward of the dose ring 65, and the movement is controlled, for example, by using a helical shaped guiding track 78 which is, preferably arranged next to each row of the powder chambers 66. The dose ring 65 can thus provide space for e.g. 60 doses, or more, within a total dose ring diameter of 85 mm.

FIG. 22A, displays an alternative design where the uncovering device 79 is pressed, radially inward towards the center of the dose ring 65, by a spring 80. A circular shaped cam 81 arranged in the surface of the dose ring 65 prevents the uncovering device 79 to move inwards towards the center of the dose ring 65. The uncovering device 79 is initially situated in a radial position over the outer line of powder chambers 66. Thus, at inhalation, the outer line of powder chambers 66 is the first to be emptied. At the toggle point 82 the cam 81 is ends/is missing and the uncovering device 79 can radially jump, under the effect of the spring 80, to a position over the inner line of the powder chambers in the dose ring 65. The spring 80 is displayed in FIG. 8A in two different positions, before and after the described toggle point 82. The position of the spring 80, after the described toggle point 82, is displayed with a dashed line on the same figure.

FIG. 22B displays the dose ring 65 viewed from above where the two positions of the spring 80, described in FIG. 8A, are displayed a bit more clearly. One of the positions of the spring 80, after the toggle point (not shown) is also here indicated with a dashed line.

FIG. 23A shows an alternative design, where the uncovering device takes the form of a lid 83 which can move radially over the powder chambers 66. The figure shows the lid 83 positioned over the inner line of powder chambers 66. This allows the airflow 72 to pass over the outer line of the powder chambers 66 and empty one powder chamber at a time. The position of the lid 83 can be controlled by a guiding pin (not shown) arranged in the lid 83 combined with guiding tracks arranged in dos ring surface or a spring with a restrictive cam as described above.

FIG. 23B shows the lid 83 positioned over the outer line of the powder chambers. This position allows the airflow 72 to pass over the inner line of powder chambers 66 and there empty one powder chamber at a time.

The description above is primarily intended to facilitate the understanding of the invention, but is of course not limited to the specified designs; also other variants of the invention are possible and conceivable within the framework of the innovative idea and the scope of protection of the subsequent claims.

The invention claimed is:

1. An inhalation device comprising:
a plurality of powder chambers for storing a respective dose of preloaded powdery substance;
a housing including an air channel for dispensing one dose at a time;
an advancing mechanism arranged to feed a dose ring in a direction of rotation to align one respective powder chamber with the air channel at a time;
wherein the powder chambers are oriented in a surface of the dose ring;
at least one seal located between the housing and the dose ring, and the at least one seal is arranged to seal the dose ring so that the powder chambers are sealed from each other for retaining the doses of powder in the powder chambers;
at least one flap located within the seal; and
wherein the air channel, in a region of the flap, includes a first cross-sectional area and a second cross-sectional area, wherein the first cross-sectional area is smaller than the second cross-sectional area, and a cross-sectional area of the air channel increases along a direction of an air flow from the first cross-sectional area to the second cross-sectional area to create an underpressure in the region of the flap, and the flap is openable by the underpressure in the air channel so that the respective powder chamber is opened to at least a portion of the air channel arranged in a position for releasing the respective dose of preloaded powdery substance from the respective powder chamber, and the respective dose of preloaded powdery substance is passable through the air channel by way of the air flow.

2. The inhalation device according to claim 1, wherein the air channel is oriented substantially transverse to the direction of rotation of the dose ring and is arranged in the housing, wherein the housing is adjacent to the dose ring and rotationally fixed with respect to the dose ring, and the flap, at the position for releasing the dose of powder, is open towards the housing.

3. The inhalation device according to claim 1, wherein a length and width of the air channel, at the position for releasing the dose of powder, is arranged to at least substantially cover the respective powder chamber.

4. The inhalation device according to claim 1, wherein a one way valve is arranged in the housing.

5. The inhalation device according to claim 1, wherein the air flow through the air channel passes the powder chamber, opened to the air channel, and pulls the respective dose of preloaded powdery substance out through a mouthpiece.

6. The inhalation device according to claim 1, wherein an advancing arm at one end is provided with a cog formed segment which at activation of the advancing mechanism engages with a cog of a cog ring arranged in the dose ring to advance one of the respective doses of preloaded powdery substance.

7. The inhalation device according to claim 1, wherein the advancing arm and/or the cog formed segment are arranged, along a feed return, to spring away from the cog ring of the dose ring.

8. The inhalation device according to claim 1, wherein the dose ring is arranged as a large cog ring and the advancing arm is provided with a segment of a small cog wheel,
that a gear ratio is provided so that a respective powder chamber is moved to the position for releasing the respective dose of preloaded powdery substance at substantially half a flip up motion, and
that the cog formed segment of the advancing arm, in the flip up position, clears from the cog ring of the dose ring where a rotation of the dose ring stops.

9. The inhalation device according to claim 1, wherein the dose ring is arranged to form at least one part of the housing.

10. The inhalation device according to claim 1, wherein the dose ring and an upper housing are attached to each other by means of clips.

11. The inhalation device according to claim 1, wherein an outer shape of the housing is substantially rectangular.

12. The inhalation device according to claim 1, wherein an outer shape of the housing is substantially circular.

13. The inhalation device according to claim 1, wherein the seal between the dose ring and the housing is integrated in the housing.

14. The inhalation device according to claim 1, wherein the seal between the dose ring and the housing is integrated in the dose ring.

15. The inhalation device according to claim 1, wherein the air channel is arranged as a spiral in an immediate vicinity of holes in an inlet for inflowing air.

16. The inhalation device according to claim 1, wherein the seal is arranged to rotate with the dose ring and is provided with at least a plurality of flaps corresponding to a number of powder chambers in the dose ring.

17. The inhalation device according to claim 1, wherein the seal is arranged to be rotationally fixed to the housing and is provided with at least one flap.

18. The inhalation device according to claim 1, wherein the flap is arranged to open automatically by means of the underpressure created in the air channel when the air flow is in an intended direction through the air channel.

19. The inhalation device according to claim 1, wherein the powder chambers are oriented in the surface of the dose ring so that at least one powder chamber is arranged radially inside of another powder chamber, and that an uncovering device is arranged to move along the surface of the dose ring in substantially radial direction, transversely to the direction of rotation of the dose ring, and thereby be located over one of the powder chambers at a time so that the respective dose of preloaded powdery substance is exposed and released.

20. The inhalation device according to claim 19, wherein a guiding pin in the uncovering device is arranged to run in a guiding track arranged in the dose ring and arranged so that the uncovering device is automatically positioned in a radial direction of the dose ring.

21. The inhalation device according to claim 1, wherein the powder chambers are oriented in the surface of the dose ring in two or more substantially circular rows.

22. The inhalation device according to claim 1, wherein the powder chambers are oriented in the surface of the dose ring in a helical formed row.

23. An inhalation device comprising:
- a dose ring including a plurality of powder chambers on a surface of the dose ring, the plurality of powder chambers configured for storage of a respective dose of a preloaded powdery substance;
- a housing including an air channel configured for dispensing the respective dose of the preloaded powdery substance;
- an advancing mechanism configured to rotate the dose ring and align a respective powder chamber of the plurality of powder chambers with the air channel;
- at least one seal located between the housing and the dose ring, the at least one seal isolates each powder chamber of the plurality of powder chambers from each other and retains the preloaded powdery substance in each powder chamber; and
- at least one flap located within the seal, the flap including a first end attached to the seal and a separated surface moveable with respect to the seal, and the flap is moveable between an open position and a closed position:
  - in the closed position, the separated surface lies along the seal, and
  - in the open position, the flap is configured to move from the closed position by an underpressure in the air channel to open the respective powder chamber to the air channel and release the respective dose of preloaded powdery substance to pass-through the air channel by way of an air flow.

24. The inhalation device according to claim 23, wherein the air channel, in a region of the flap, includes a cross-section that increases in area along a direction of the air flow to create an underpressure in the region of the flap.

25. The inhalation device according to claim 23, wherein the seal between the dose ring and the housing is integrated in the housing.

* * * * *